(12) United States Patent
Richard et al.

(10) Patent No.: US 10,073,038 B2
(45) Date of Patent: Sep. 11, 2018

(54) GLOW DISCHARGE SPECTROSCOPY METHOD AND SYSTEM FOR MEASURING IN SITU THE ETCH DEPTH OF A SAMPLE

(71) Applicant: HORIBA JOBIN YVON SAS, Longjumeau (FR)

(72) Inventors: Simon Richard, Palaiseau (FR); Jean-Paul Gaston, Vert le Grand (FR); Olivier Acher, Gif-sur-Yvette (FR); Patrick Chapon, Villebon sur Yvette (FR)

(73) Assignee: Horiba Jobin Yvon SAS, Longjumeau (FR)

( * ) Notice: Subject to any disclaimer, the term of this patent is extended or adjusted under 35 U.S.C. 154(b) by 0 days.

(21) Appl. No.: 15/305,367

(22) PCT Filed: Apr. 28, 2015

(86) PCT No.: PCT/FR2015/051156
§ 371 (c)(1),
(2) Date: Oct. 20, 2016

(87) PCT Pub. No.: WO2015/166186
PCT Pub. Date: Nov. 5, 2015

(65) Prior Publication Data
US 2017/0045457 A1 Feb. 16, 2017

(30) Foreign Application Priority Data

Apr. 30, 2014 (FR) ..................................... 14 53997

(51) Int. Cl.
*G01N 21/67* (2006.01)
*G01N 21/68* (2006.01)
(Continued)

(52) U.S. Cl.
CPC ............. *G01N 21/67* (2013.01); *G01B 11/22* (2013.01); *G01J 3/443* (2013.01); *G01N 21/68* (2013.01);
(Continued)

(58) Field of Classification Search
CPC .................. G01N 21/67; G01N 21/68; G01N 2201/06113; G01N 2201/0612;
(Continued)

(56) References Cited

U.S. PATENT DOCUMENTS

2002/0071117 A1* 6/2002 Ukon ...................... G01J 3/443
356/316
2002/0183940 A1* 12/2002 Chapon .................. G01N 21/67
702/23
(Continued)

FOREIGN PATENT DOCUMENTS

FR 2843801 2/2004
JP 2002048519 2/2002
(Continued)

OTHER PUBLICATIONS

"Etch Rate Monitor", IBM Technical Disclosure Bulletin, International Business Machines Corp. (Thornwood), US, vol. 29, No. 5, Oct. 1, 1986, p. 2204, XP000806288.
(Continued)

*Primary Examiner* — Dominic J Bologna
(74) *Attorney, Agent, or Firm* — Young & Thompson; Eric Jensen; Roland Long

(57) ABSTRACT

A glow discharge spectrometry system includes a glow discharge lamp suitable for receiving a solid sample (10) and forming a glow discharge etching plasma (19). The system (100) for measuring in situ the depth of the erosion crater generated by etching of the sample (10) includes an optical separator (3), optical elements (4) suitable for directing a
(Continued)

Figure 1:
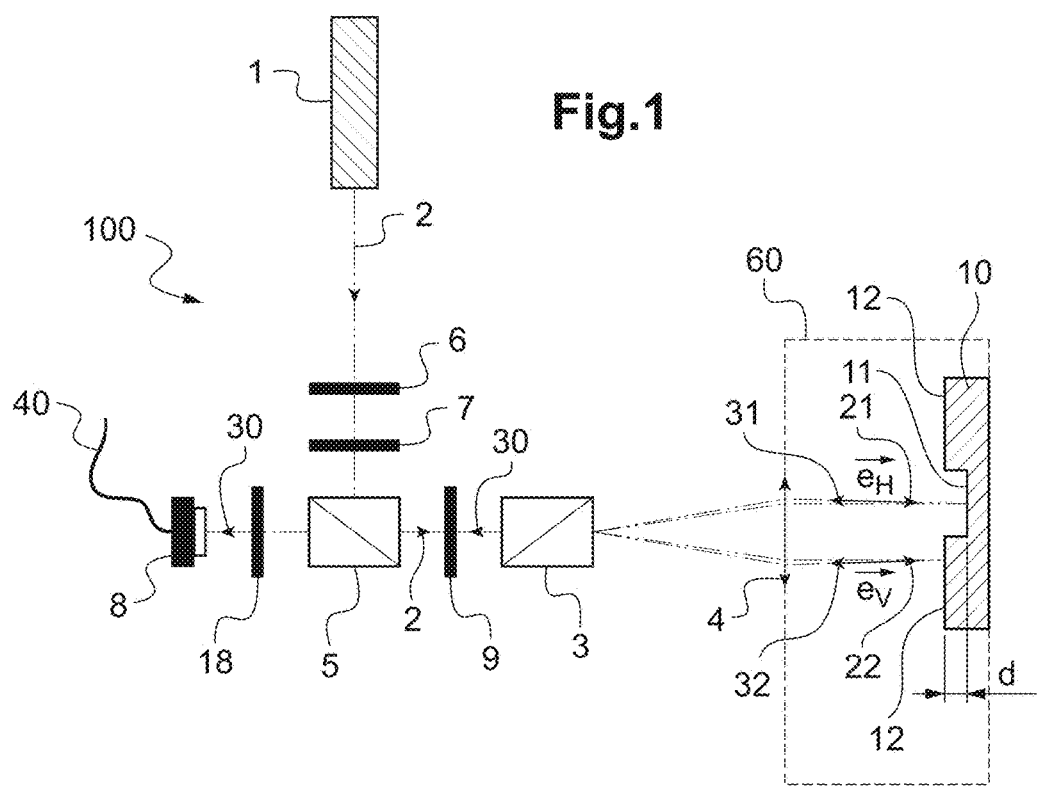

first incident beam (21) toward a first zone (11) of the sample, the first zone being exposed to the etching plasma, and a second incident beam (22) toward a second zone (12) of the same side of the sample, the second zone being protected from the etching plasma, respectively, and an optical recombining device (3) suitable for forming an interferometric beam (30) so as to determine the depth (d) of the erosion crater.

20 Claims, 3 Drawing Sheets

(51) Int. Cl.
    *G01B 11/22*      (2006.01)
    *G01J 3/443*      (2006.01)
    *H01J 37/32*      (2006.01)

(52) U.S. Cl.
    CPC .. *H01J 37/32018* (2013.01); *H01J 37/32963* (2013.01); *H01J 37/32972* (2013.01); *G01N 2201/0612* (2013.01); *G01N 2201/06113* (2013.01); *H01J 2237/334* (2013.01)

(58) Field of Classification Search
    CPC ................ G01B 11/22; H01J 37/32018; H01J 37/32972; H01J 37/32963; H01J 2237/334

See application file for complete search history.

(56) References Cited

U.S. PATENT DOCUMENTS

2005/0287815 A1    12/2005   Lai et al.
2013/0314692 A1    11/2013   Goto et al.

FOREIGN PATENT DOCUMENTS

JP      2002129364     5/2002
WO    2012077652     6/2012

OTHER PUBLICATIONS

Amary et al.: "A new sensor for trench depth monitoring: the TDM 200", Proceedings of SPIE, International Society for Optical Engineering, US, vol. 5343, No. 1, Jan. 1, 2003, pp. 244-254, XP002356930.

* cited by examiner

GLOW DISCHARGE SPECTROSCOPY METHOD AND SYSTEM FOR MEASURING IN SITU THE ETCH DEPTH OF A SAMPLE

TECHNICAL FIELD TO WHICH THE INVENTION RELATES

The present invention relates to the devices and methods for glow discharge (GD) elementary analysis, by optical emission spectrometry (GD-OES) or by mass spectrometry (GD-MS).

More precisely, the invention relates to a device and a method of glow discharge spectrometry (GDS) adapted to measure in situ the etching depth of a sample exposed to this glow discharge plasma.

The invention applies in particular to a system or a method for the analysis of materials by glow discharge spectrometry, this analysis being resolved as a function of the etching depth in the sample.

TECHNOLOGICAL BACK-GROUND

The glow discharge spectrometry is a technic of analysis that allows analysing the elementary and/or molecular chemical composition of homogeneous or multi-layer solid samples. The measurement may be made deep inside a sample or be depth-resolved.

The glow discharge spectrometry is commonly used to analyse the composition or the composition profile of solid samples.

The principle of glow discharge spectrometry consists in exposing a limited zone of a face of a sample to an etching plasma. The plasma extracts atoms from the surface of the sample, and places them in ionized or excited electronic states. The nature of these atoms is determined by analysis of their emission spectrum in the plasma, or of the mass spectrum of the ions produced in the plasma. As the atoms are extracted, a crater is formed at the surface of the sample as a function of the time of exposure to the plasma. An analysis of the signals detected by spectrometry as a function of the time of erosion hence allows obtaining the composition of the sample resolved as a function of the etching time.

However, the etching rate generally varies during the etching method. The etching rate varies in particular as a function of the composition of the sample zone that is exposed to the plasma and also as a function of transitory phenomena linked to the starting of the plasma.

Now, it is desirable to analyse the composition as a function of the depth of the erosion crater generated by the plasma, and not only as a function of time during the erosion plasma.

There now exist different methods for determining the depth of the erosion crater as a function of time.

The most used method today is based on a calibration of the erosion rate for reference samples of known composition. This calibration requires the making of different measurements on different reference samples and supposes hypotheses such as, for example, a known and/or homogeneous density. The accuracy of the result obtained remains uncertain.

Other methods of analysis by glow discharge spectrometry and simultaneous determination of the etching depth have been proposed.

The patent document WO 2007/113072_A1 describes a method of determination of a variation of height due to the erosion of the surface of a sample exposed to an etching plasma in a GDS device. The method described is based on the use of a chromatic confocal movement sensor, which detects a variation of position of the plane of the sample surface with respect to the initial position thereof before the starting of the plasma.

The patent document CN102829732 describes another device for responding to the same technical problem, based on a triangulation sensor. In this case, the sensor measures the position of a laser beam reflected by the surface, the depth of which is desired to be known.

On the other hand, the patent document U.S. Pat. No. 6,784,989 or FR 2843801 of HORIBA Jobin Yvon describes the use of a two-wave laser interferometer. According to this document, an optical beam is split into two secondary beams, one of the secondary beams being reflected on the surface of the sample exposed to the etching plasma, and the other secondary beam being reflected on a fixed reference surface, external to the sample. The optical recombination of the two reflected beams forms an interferometric beam, which varies as a function of the etching depth in the sample.

However, all these optical methods of measurement are sensitive to the heating induced by the etching plasma, which produces an expansion of the glow discharge chamber. A bias may hence be introduced, because it is not possible to differentiate the erosion of the crater and the expansion of the plasma chamber. These methods of erosion depth determination have hence a limited accuracy and do not permit in practice to reach a level of accuracy lower than one micron.

Moreover, the triangulation optical devices generally require an optical window with plane and parallel faces, sometimes of great size, to let the optical beams pass through. However, an apparatus of glow discharge by optical emission spectrometry (GD-OES) generally includes a plasma chamber having an axial opening of limited size and tightly closed by a lens intended to collect the optical emission flow and not by a planar window.

The replacement of the optical emission flow collection lens by a planar window would imply a significant reduction of the optical emission signal collected, and hence a loss of accuracy of the emission spectrometry measurements.

There thus exists a need for a system and a method for measuring the etching depth of a sample in a glow discharge spectrometry device, which is accurate and which does not affect the glow discharge spectrometry signals.

OBJECT OF THE INVENTION

The present invention has for object to remedy the drawbacks of the prior systems and proposes more precisely a system of glow discharge spectrometry and in situ measurement of the etching depth of a sample comprising a glow discharge lamp adapted to receive a solid sample and to form a glow discharge etching plasma, the sample having, on a same face, a first zone exposed to the etching plasma and a second zone protected from the etching plasma; a spectrometer coupled to the glow discharge lamp, the spectrometer being adapted to measure, as a function the time of exposure of the first zone to said plasma, at least one signal representative of the glow discharge plasma by optical emission spectrometry and/or by mass spectrometry of said glow discharge plasma, and a system of in situ measurement of the depth of the erosion crater generated by etching of the first zone of the sample as a function of the time of exposure to said plasma.

According to the invention, the measurement of the etching depth takes as a null-depth reference, at each instant, the second zone of the sample, not exposed to the plasma. That way, the measurement is made insensitive to the expansions of the etching chamber.

According to the invention, the measurement system of the erosion crater depth includes a light source adapted to emit a light beam; an optical splitter adapted to spatially or angularly split the light beam into a first incident beam and a second incident beam; the glow discharge lamp (60) is adapted to provide a first optical path towards the first zone and a second optical path towards the second zone of the sample; optical means adapted to direct, respectively, the first incident beam towards the first zone along the first optical path and the second incident beam towards the second zone along the second optical path, so as to form a first reflected beam by reflection on the first zone and, respectively, a second reflected beam by reflection on the second zone, an optical recombination device adapted to recombine the first reflected beam and the second reflected beam and to form an interferometric beam; detection means adapted to receive the interferometric beam and to detect an interferometric signal as a function of the time of exposure of the first zone to said plasma; processing means adapted to process the interferometric signal so as to determine the depth (d) of the erosion carter as a function of the time of exposure of the first zone to said plasma, by taking as a null-depth reference the second zone, not exposed to the plasma.

According to a particular and advantageous aspect of the invention, the detection means and the processing means are adapted to process the interferometric signal and to extract therefrom a measurement of the amplitude (A) and of the phase (PHI) of the interferometric signal as a function of the time of exposure of the first zone to said plasma.

Preferably, the first incident beam forms an angle of incidence lower than ten degrees with respect to the normal to the surface of the first zone of the sample, and preferably non zero and approximately equal to five degrees.

Advantageously, the sample forms the cathode of the discharge lamp and the discharge lamp includes a cylindrical anode having a first axial opening adapted for the passage of the first incident beam and of the first reflected beam, and the anode includes a second opening, offset with respect to the axis of the anode, the second opening being provided with an optical window adapted for the passage of the second incident beam and of the second reflected beam.

According to an aspect of the invention, the optical splitter comprises at least one polarization-splitting prism.

Preferentially, the optical splitter comprises a Wollaston prism, the optical recombination device comprises another Wollaston prism, and the optical means adapted to direct, respectively, the first incident beam towards the first zone and the second incident beam towards the second zone comprise a lens optical system, said Wollaston prisms being arranged in the focal plane of this lens optical system.

In a particular embodiment, the optical splitter and the optical recombination device are merged together.

In one embodiment, the spectrometer comprises a mass spectrometer coupled to the discharge lamp via an opening, the mass spectrometer being adapted to measure at least one signal representative of ionised species of the glow discharge plasma by mass spectrometry.

In another embodiment, the spectrometer comprises an optical spectrometer coupled to the discharge lamp via an optical window or via a lens optical system, the optical spectrometer being adapted to measure at least one optical emission signal representative of excited species of the glow discharge plasma, preferably in a direction normal to the surface of the first zone of the sample.

According to a particular aspect of this embodiment, the glow discharge spectrometry system includes an optical spectrometer adapted to measure at least one optical emission signal representative of excited species of the glow discharge plasma, and the light source is adapted to emit a light beam at a wavelength selected outside of a range of wavelengths of atomic rays of optical emission of the glow discharge plasma.

In a particular and advantageous variant, the detection means comprise a polarimeter adapted to measure at least one polarized component of the interferometric beam.

Particularly advantageously, said polarimeter comprising other optical splitting means arranged so as to split the interferometric beam into a plurality of polarized components and a plurality of detectors adapted to each detect respectively a polarized component of the plurality of polarized components of the interferometric signal.

The invention also relates to a method of glow discharge spectrometry and in situ measurement of the etching depth of a sample, comprising the following steps:

placing a solid sample into a glow discharge lamp, the sample having, on a same face, a first zone exposed to an etching plasma and a second zone protected from the etching plasma;

detection and analysis by optical emission spectrometry and/or by mass spectrometry of at least one signal representative of excited and/or ionized species of the glow discharge plasma, as a function of the time of exposure of the first zone to said plasma;

emission of a light beam;

spatial or angular split of the light beam into a first incident beam and a second incident beam;

orientation, respectively, of the first incident beam towards the first zone along a first optical path and of the second incident beam towards the second zone along a second optical path, so as to form a first reflected beam by reflection on the first zone and, respectively, a second reflected beam by reflection on the second zone;

optical recombination of the first reflected beam and of the second reflected beam and to form an interferometric beam;

detection of the interferometric beam to form at least one interferometric signal as a function of the time of exposure of the first zone to said plasma; and processing of the at least one interferometric signal to extract therefrom a measurement of the erosion crater depth as a function of the time of exposure of the first zone to said plasma.

According to a particular aspect, the method of in situ measurement of the etching depth of a sample further comprises the following steps:

processing of the interferometric signal to extract therefrom a measurement of the phase (PHI) of the interferometric signal as a function of the time of exposure of the first zone to said plasma, determination, at each instant t, of an instantaneous etching rate $V_e$ of the first zone of the sample, by application of the following formula:

$$V_e = \frac{LAMBDA}{4 \times \pi} \times \frac{dPHI}{dt}$$

where LAMBDA represents the wavelength of the light source and dPHI/dt the differential coefficient of the phase (PHI) of the interferometric signal measured with respect to time.

According to a particular and advantageous embodiment, the etching plasma operates in a pulsed mode, by alternation of a phase in which the plasma is switched-on and another phase in which the plasma is switched-off, and the method of in situ measurement of the etching depth comprises the following steps:

the detection of the at least one interferometric signal is triggered during the phases in which the plasma is switched-on and/or, respectively, during the phases in which the plasma is switched-off, so as to differentiate an interferometric signal associated with the phases in which the plasma is switched-on from another interferometric signal associated with the phases in which the plasma is switched-off;

processing of the interferometric signal associated with the phases in which the plasma is switched-on and/or, respectively, of the other interferometric signal associated with the phases in which the plasma is switched-off so as to correct the measurement of the erosion crater depth from the drifts induced during the phases in which the plasma is switched-on and/or, respectively, during the phases in which the plasma is switched-off.

The present invention also relates to the characteristics that will be revealed in the following description and that will have to be considered in isolation or according to any of their technical possible combinations.

Figure 2:
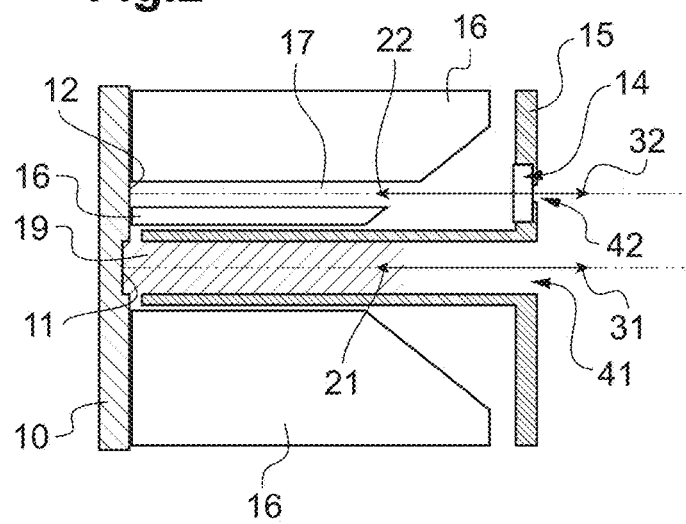
Figure 3:
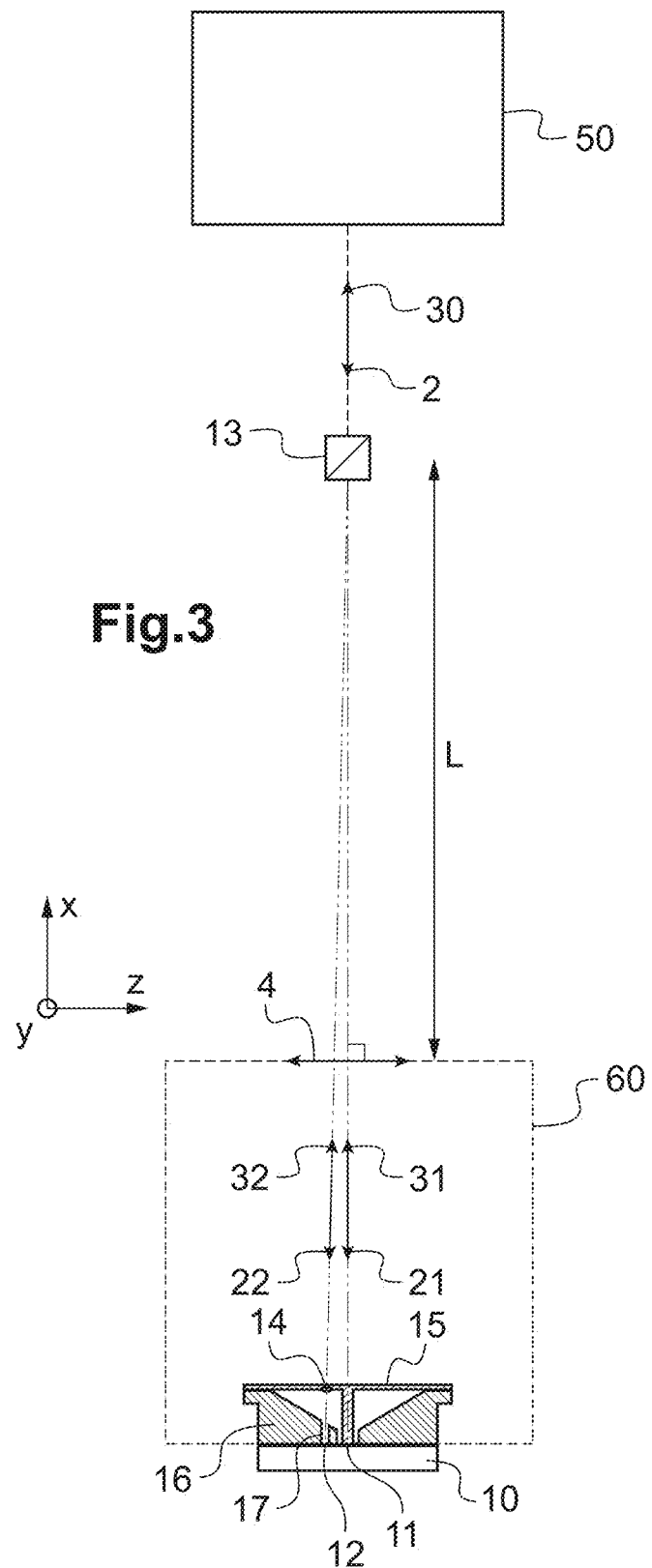
Figure 4:
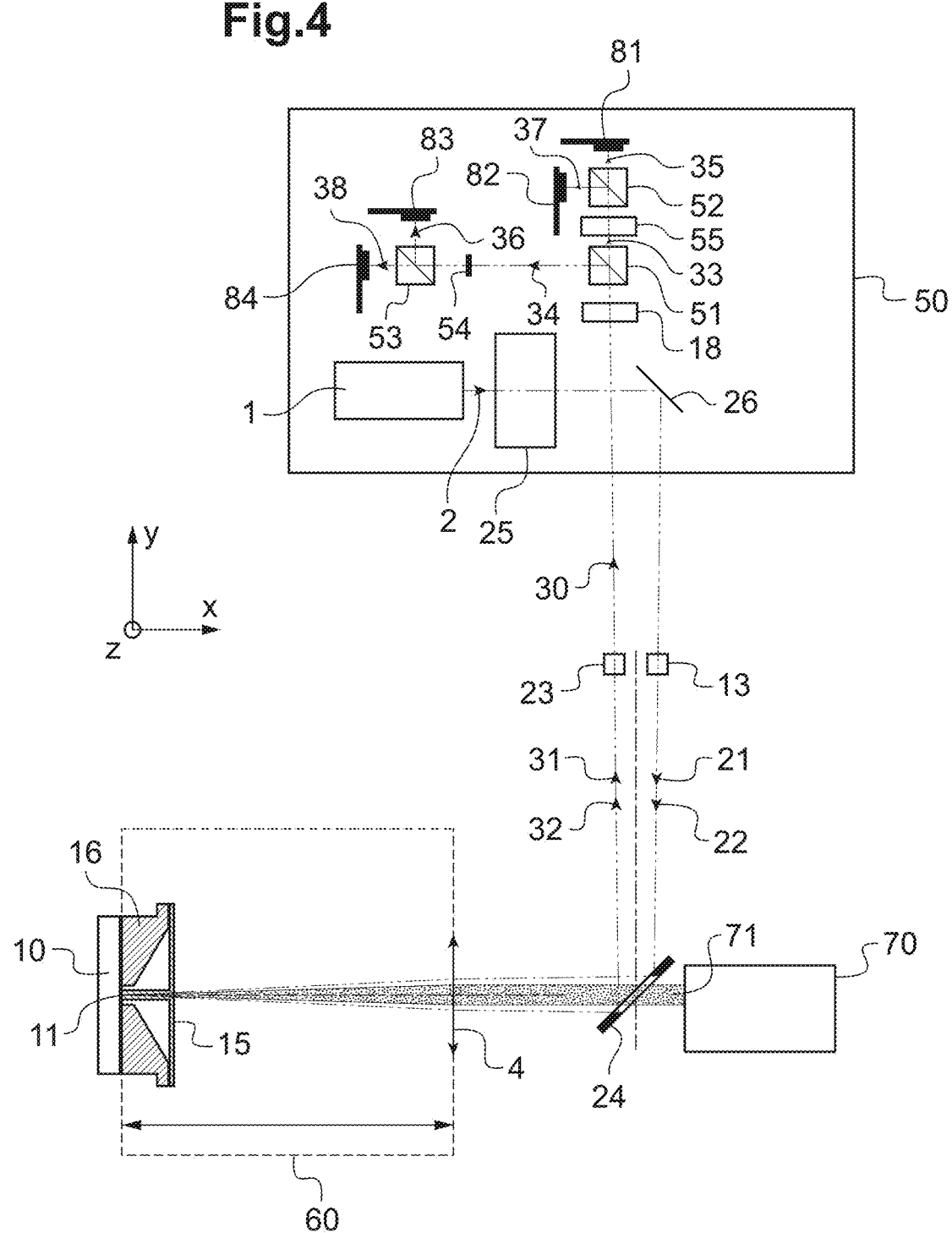

This description, given by way of non-limitative example, will allow to better understand how the invention may be performed with reference to the appended drawings, in which:

FIG. 1 schematically shows a system of in situ measurement of the etching depth of a sample in a glow discharge spectrometry apparatus according to one embodiment by optical emission spectrometry;

FIG. 2 schematically shows a sectional view of a suitable glow discharge lamp according to an exemplary embodiment;

FIG. 3 schematically shows another example of a system of in situ measurement of the etching depth of a sample in an apparatus of glow discharge spectrometry by optical emission spectrometry;

FIG. 4 schematically shows an example of a system of in situ measurement of the etching depth of a sample in an optical-emission glow discharge spectrometry apparatus according to another embodiment.

DEVICE

FIG. 1 schematically shows a system of in situ measurement of the etching depth of a sample in a glow discharge spectrometry (GDS) apparatus.

A sample 10 that is located in a plasma chamber of a glow discharge spectrometry device 60 is shown.

By way of example, the lens 4 tightly closes an opening, for example axial, in the etching chamber of the GDS device.

The sample has a face, a first zone 11 of which is exposed to the etching plasma, whereas another zone 12 is protected from this same etching plasma.

The principle of the in situ measurement of the etching depth is based on the integration of an optical interferometric device. Advantageously, the optical components of this interferometer are arranged outside the plasma chamber of the discharge lamp.

The interferometer essentially includes a light source, an optical beam splitter 3 that splits the source beam into two beams propagating along two separated optical paths, an optical beam combiner that recombines the previously split beams, a source-detector splitter 5, a detector 8 and a signal processing system.

The example of FIG. 1 illustrates an example of an optical interferometer operating in polarized light.

More precisely, the measurement system comprises a source 1, which is for example a laser source or a laser diode. The light source 1 emits a light beam 2, preferably monochromatic, for example at a wavelength of 635 nm, or of 780 nm, 532 nm, 405 nm. In the example of FIG. 1, a diaphragm 6, or source hole, is arranged so as to limit the spatial extent of the source beam 2. A half-wave plate (also called λ/2 plate) 7 allows determining the axis of polarization of the source beam.

A source-detector splitter 5, for example of the polarization-splitting cube type, is arranged on the source beam 2. The orientation of the axis of the half-wave plate 7 with respect to the axes of the splitter 5 allows adjusting the power of the source beam 2. Preferably, the polarization axis of the polarizer 7 is oriented so that the split incident beams 21, 22 have the same amplitude. The detected interferometric beam has a maximum intensity when the amplitude of the beams that are recombined together is equal.

In the example of FIG. 1, the source-detector splitter 5 directs the source beam 2 towards a λ/2 plate (reference sign 9 in FIG. 1), then towards another optical beam splitter 3. Advantageously, the λ/2 plate is oriented so that the split incident beams 21, 22 have the same amplitude. The detected interferometric beam has a maximum interferometric contrast when the amplitude of the beams that are recombined together is equal. The optical splitter 3 is for example a polarization-splitting cube, whose polarization axes are inclined by 45 degrees with respect to the axis of the linearly-polarized incident beam 2, that has passed through the λ/2 plate. By way of example, optical splitter 3 is a Wollaston prism that is adapted to angularly split the incident beam into two incident beams 21, 22, linearly polarized according to polarization states that are orthogonal relative to each other. Hence, a first, p-polarized incident beam 21 is directed in a first direction and a second, s-polarized incident beam 22 is directed in a second direction. By construction of the Wollaston prism 3, the first direction and the second direction are angularly separated by an angle comprised between 0.1 and 20 degrees.

The lens 4 is mounted on an opening of the discharge lamp so as to ensure the vacuum tightness while allowing an optical access inside the discharge lamp. Preferably, the optical splitter 3 is arranged at the focus of the lens 4. Hence, the lens 4 forms two spatially-split incident beams 21, 22, that propagate parallel to each other in the discharge lamp 60 towards one face of the sample.

The small spatial spacing of the incident beams 21 and 22 allows coupling them to the discharge lamp via the already present lens 4. It is hence not necessary to perform a new optical opening in the chamber of the discharge lamp 60 for the passage of two separated optical beams 21 and 22.

In a variant, instead of Wollaston prisms, it is possible to use beam offset splitters and to replace the lens 4 by a window.

Preferably, the sample has a planar face that is intended to be exposed partially to the etching plasma. The discharge lamp 60 is adapted to allow the first incident beam 21 to follow a first optical path towards a first zone 11 of the sample, which is intended to be exposed to the plasma. On the other hand, the lamp is specially adapted to allow the second incident beam 22 to follow a second optical path towards a second zone 12 of the sample, which however remains protected from the etching plasma.

Hence, the lens 4 focuses the first incident beam 21 on the first zone 11 of the sample, that is exposed to the etching plasma. On the other hand, the lens 4 focuses the second incident beam 22 on the second zone 12 of the sample that is protected from the etching plasma.

An example of discharge lamp specially adapted to allow these two optical paths is described in the present document in connection with FIG. 2.

By reflection on the first zone 11, the first incident beam 21 forms a first reflected beam 31. Similarly, by reflection of the second zone 12, the second incident beam 22 forms a second reflected beam 32. In the example illustrated in FIG. 1, the sample has a planar surface and the etching of the first zone 11 generates a flat-bottom crater. Moreover, in this example, the incident beams 21, 22 are reflected on the sample under a zero incidence angle. In this case, the first reflected beam 31 propagates in the direction opposite to the first incident beam 21 and, respectively, the second reflected beam 32 propagates in the direction opposite to the first incident beam 22.

The lens 4 collects the first reflected beam 31 and the second reflected beam 32, and directs them towards an optical recombination system, which is herein the same Wollaston prism 3 having served to split the incident beam.

The Wollaston prism recombines the first reflected beam 31 and the second reflected beam 32 to form an interferometric beam 30. The interferometric beam passes through the λ/2 plate and is incident on the source-detector polarizing splitter 5 that sends a polarization component of the interferometric beam towards a filter 18 and a detector 8. As indicated hereinabove, the orientation of the plate 9 is such that the polarization of the incident beam 2 is at 45° with respect to the axes of the Wollaston prism 3. This arrangement has for beneficial effect that the couple consisted by the plate 9 and the splitter 5 forms, in the direction of return, a polarization analyser at 45° of the axes of the Wollaston prism 3, which effectively allows generating an interferometric signal by summation of the amplitudes of the beams 31 and 32.

The filter 18 is a spectral filter, preferably centred on the emission wavelength of the light source 1. The filter 18 allows eliminating the spurious light coming from the plasma or from the ambient lighting. The filter 18 is for example an interferential filter centred to 635 nm, of spectral width 10 nm.

The detector 8 detects an interferometric signal 40 as a function of time. A processing system allows numerically processing this interferometric signal 40 so as to extract therefrom information about the amplitude and phase of the interferometric signal.

During the etching of the first zone 11 of the sample, the first optical path becomes longer, whereas the second optical path remains stable. The difference of optical path hence increases as a function of the etching of the first zone 11 of the sample. Hence, the detector detects an interferometric signal 40 whose intensity is representative of the etching depth of the first zone 11 of the sample. The first optical path forms the measurement arm of the interferometer: it goes from the beam splitter-combiner 3 to the first zone 11 of the sample and comes back to the beam splitter-combiner 3. The second optical path forms the reference arm of the interferometer: it goes from the beam splitter-combiner 3 to the second zone 12 of the sample and comes back to the beam splitter-combiner 3.

In a manner otherwise known, in the case of an opaque and homogeneous sample, the analysis of the interferometric signal allows determining the etching depth in the sample. Indeed, in this case, the interferometric signal has a sinusoidal shape as a function of time. The number of periods of the intensity curve allows determining the etching depth, knowing the source beam wavelength. The error of so-obtained depth interferometric measurement is of the order of $\lambda/8$, where $\lambda$ is the source beam wavelength.

During the spraying of the sample, the depth of the crater increases and hence the phase difference between the two reflected waves 31, 32 varies as a function of time t.

More precisely, let's note $\delta(t)$ the relative phase-shift between the first reflected beam 31 and the second reflected beam 32.

$$\delta(t) = 2kd(t) + \varphi_H - \varphi_V$$

where $k = 2\pi/\lambda$, $d(t)$ represents the etching depth as a function of time.

The reflection coefficient $r_V$ on the first zone 11 and the reflection coefficient $r_H$ on the second zone 12 are expressed by the following relations:

$$r_V = \rho_V \exp(i\varphi_V)$$

$$r_H = \rho_H \exp(i\varphi_H)$$

Let's note I(t) the intensity of the interferometric beam as a function of time, $E_V$ the amplitude of the electric field relating to the incident beam 21 on the first zone 11, i.e. in the crater, $E_H$ the amplitude of the electric field relating to the incident beam 22 on the second zone 12. The intensity of the detected interferometric signal is written according to the following relation:

$$I(t) = \tfrac{1}{2}(E_V^2 \rho_V^2 + E_H^2 \rho_H^2 + 2E_V E_H \rho_V \rho_H \cos(\delta(t)))$$

If the etching rate is constant, the optical path difference increases linearly and hence the detected intensity varies sinusoidally as a function of time. In the case of an homogeneous material, the result of a series of interferometric measurements as a function of time is then a set of points on a sinusoidal curve. For a sample including a multilayer stack of different materials, the etching rate generally depends on the composition of each layer. If the layers are opaque, the series of measured points forms by interpolation an experimental curve that is consisted of pieces of sinusoids of different periods.

To determine the depth d(t) of the etched crater, the number of detected periods from the beginning of the etching is estimated. Indeed, a complete period of sinusoid is equivalent in terms of length to a wavelength λ of the light source (for example, the laser) used. Now, the difference of optical path between the two waves is at each instant equal to the double of the depth of the etched crater. Each period on the intensity curve hence corresponds to an etched depth equal to λ/2.

Between the beginning of the etching and an instant t, if the number of periods on the intensity measurement curve I(t) is equal to an integer number N, then the etched depth of the crater is equal to N*λ/2.

For an homogeneous sample, a simple visual estimation of the number of periods on the intensity curve of the interferometric signal I(t) hence allows determining the etching depth with an accuracy of the order of λ/8, which corresponds in the case of the laser used to about 80 nm. For a better accuracy, it is also possible to determine the frequency of the intensity curve by using a fit, for example a sinusoidal function. This allows obtaining a still more important accuracy on the etching depth.

However, in the case where the sample includes a stack of thin and/or transparent layers, the measurement of the signal of intensity I(t) of the interferometric beam as a function of time offers only limited accuracy and sensitivity.

Generally, the plasma chamber of a discharge lamp has only one optical access allowing an optical path, usually limited, to the first zone 11 exposed to the etching plasma. The patent document FR1250594 describes an example of glow discharge lamp including a hollow cylindrical anode and a single optical access on the axis of the anode.

FIG. 2 schematically shows a sectional view of a discharge lamp specially adapted to an interferometric system according to an exemplary embodiment.

The discharge lamp includes an anode 15, a cathode formed by the sample 10 itself, and an electrically insulating part 16 arranged between the anode 15 and the sample 10. The anode 15 has a generally cylindrical shape illustrated in FIG. 2 in section along the axis of the cylinder. The electrically insulating part 16 has also a cylindrical shape and includes a coaxial cylindrical opening in which is inserted the anode. The part 16 allows positioning accurately the anode with respect to the cathode. The tubular end of the anode 15 is hence positioned at a few tenths of millimeters from the surface of the sample. The plasma carrier gas, which is generally a rare gas, is injected into the anode, and the gases are evacuated through the space between the end of the anode and the surface of the sample. The accurate positioning of the anode 15, of the insulating part 16 and of the sample 10 allows confining the plasma in the tubular central zone inside the anode. The insulating part 16 is generally in contact with the face of the sample outside the zone 11 exposed to the etching plasma so as to protect the face of the sample outside the first zone 11. The discharge lamp hence allows a plasma 19 to selectively etch the first zone 11 of the sample that is opposite to the tubular end of the anode 15.

The axial opening 41 of the anode provides a first optical path towards a first zone 11 of the sample that is exposed to the plasma 19. By reverse return, the first reflected beam 31 under normal incidence on the first area 11 propagates along the same optical path. In the case of the optical emission spectrometry, this first optical path is also used to collect an optical emission beam emitted by the plasma 19.

In the example illustrated in FIG. 2, the discharge lamp is specially adapted to provide a second optical path towards a second zone 12 of the sample that is protected from the plasma 19. More precisely, on the one hand, an opening 42 that is provided with an optical window 14, has been formed in the anode 15, and on the other hand, an opening 17 has been formed in the insulating part 16. The opening 42 and the opening 17 are aligned, for example, along an offset axis, preferably parallel to the axis of the anode 15. Hence, the axial opening 41 and the off-axis opening 17 do not communicate between each other. The window 14 limits the leakages of gas and/or of the plasma towards the second zone 12 of the sample. The window 14 is for example a glass plate with plane and parallel faces.

The opening 42, the optical window 14 and the opening 17 allow directing the second incident beam 22 towards the second zone 12 of the sample.

A second optical path passing through the optical window 14 and going up to a second zone 12 of the sample that remains protected from the etching plasma 19 is hence defined. The second incident beam 22 may from then on be directed, through the window 14 and the opening 17, towards the second zone 12 of the sample, which is spatially separated from the first zone 11, but located on the same face of the sample 10.

The second reflected beam 32 follows preferably the second optical path in the opposite direction, towards the optical window 14.

Hence, the first beam and the second beam follow separated optical paths, while being reflected on a same face of the sample.

This configuration allows limiting the drifts of the interferometric signal due to the expansions of the discharge lamp induced by the heating of the plasma.

FIG. 3 illustrates another example of system of in situ measurement of etching depth of a sample in a glow discharge spectrometry apparatus.

The system includes a block 50 that comprises at least one light source and at least one detector located outside a discharge lamp 60.

The discharge lamp 60 comprises a cylindrical anode 15, of hollow tubular section, an electrically insulating part 16 and a sample 10 forming the cathode of the discharge lamp. A lens 4 is for example placed on an opening of the vacuum chamber of the discharge lamp 60. Preferably, the lens 4 is arranged on the axis of the anode 15.

The anode 15 is similar to that described in connection with FIG. 2. This anode 15 is of cylindrical shape and includes an axial opening forming a first optical path between the source-detector block 50 and the first zone 11 of the sample 10 that is exposed to the etching plasma.

The anode 15 of the discharge lamp includes another opening, offset with respect to the axis of the anode 15, and provided with an optical window 14. The electrically insulating part 16 arranged between the anode 15 and the sample 10 includes a cylindrical hole, so as to form a second optical path between the source-detector block 50 and the second zone 12 of the sample 10 that is protected from the etching plasma.

In the example illustrated in FIG. 3, the sample is planar, and arranged in the plane YZ of an orthonormal reference system (X, Y, Z). The normal to the plane of the sample is parallel to the axis X. It is supposed that the etching plasma generates a flat-bottom erosion crater on the first zone 11 of the sample 10.

A beam splitter-combiner 13 is arranged on the optical path of the source beam 2 between the source-detector block 50 and the discharge lamp 60. For example, the beam splitter-combiner 13 is consisted of a Wollaston prism. The Wollaston prism 13 angularly splits the incident beam 2 into a first incident beam 21 and a second incident beam 22, for example by an angle comprised between 0.1 and 10 degrees, and preferably of about 1 degree.

The beam splitter-combiner 13 is placed at a distance L from a lens 4. Preferably, the distance L is equal to the focal length of the lens 4, so that the beam splitter-combiner 13 is in the focal plane of the lens 4.

The lens 4 directs the first incident beam 21 along the axis of the anode 15, parallel to the axis X, towards the first area 11 of the sample. By reflection on this first zone 11, a first reflected beam 31 is sent back towards the lens 4.

Simultaneously, the lens 4 directs the second incident beam 22 towards the optical window 14 and the opening 17 along the second optical path towards the second zone 12 of the sample. By reflection on this second zone 12, a second reflected beam 32 is sent back towards the lens 4.

The prism 3 being in the focal plane of the lens 4, the incident beams 21 and 22 are parallel between each other and parallel to the axis X in the discharge lamp 60. Likewise, the reflected beams 31 and 32 are generally parallel between each other and parallel to the axis X in the discharge lamp 60.

The lens 4 focuses the first and second reflected beams 31, 32 on the Wollaston prism 13, which recombines them into a interferometric beam 30 towards a detector in the source-detector block 50. The arrangement of the prism 13 in the focal plane of the lens 4 allows the recombination of the first and second reflected beams 31, 32 from the geometrical point of view.

FIG. 4 schematically shows a second embodiment of a system of in situ measurement of the etching depth of a sample coupled to an optical-emission glow discharge spectrometry device.

In this second embodiment, the measurement system of the etching depth is not a simple interferometer but a polarimetric interferometer.

In FIG. 4, the same elements as those of FIG. 3 are denoted by the same reference signs.

The device of FIG. 4 includes a discharge lamp 60, a source-detector block 50 and a mirror and/or lens optical system arranged between the discharge lamp 60 and the source-detector block 50.

In the example illustrated in FIG. 4, the sample 10 is planar, and arranged in the plane YZ of an orthonormal reference system (X, Y, Z). The normal to the plane of the sample is parallel to the axis X.

The source-detector block 50 includes a light source 1, for example a laser or a laser diode. An optical isolator 25 is arranged on the source beam 2.

An optical system herein including planar mirrors 24 and 26 allows directing the source beam towards the lens 4 arranged on the axis of the discharge lamp 60.

Particularly advantageously, the mirror 26 includes an axial opening allowing the passage of an optical emission beam 71 emitted by the glow discharge plasma towards an optical emission spectrometer 70.

The system of FIG. 4 further includes a beam splitter 13 and a beam combiner 23. The beam splitter 13 is arranged on the optical path of the source beam 2. The beam combiner 23 is arranged on the optical path of the reflected beams 31, 32. For example, the beam splitter 13 is a Wollaston prism and the beam combiner 23 is another Wollaston prism. The advantage of a two-prism configuration is to allow the use of small-size prisms, which are not very bulky and not very expensive.

As a variant, as illustrated in connection with FIG. 3, the beam splitter-combiner may be consisted of a single and same prism, of greater size.

The mirror 26 reflects the source beam 2 towards the splitting prism 13. Advantageously, the mirror 26 is mounted on a plate that is adjustable in orientation about an axis OZ and an axis at 45° with respect to the axes OX and OY. The splitting prism 13 angularly splits the source beam 2 into a first incident beam 21 and a second incident beam 22. The prism 13 is constructed so that the incident beams 21 and 22 are angularly separated in a plane YZ by an angle comprised between 0.1 and 20 degrees, for example 2 degrees. The mirror 26 reflects the incident beams 21 and 22 towards the lens 4. In the example illustrated in FIG. 4, the incident beams 21 and 22 between the lens 4 and the sample are inclined with respect to the axis of the lens 4, i.e. with respect to the normal to the surface of the sample, by an angle comprised between 1 and 20 degrees in the plane XY.

The discharge lamp 60 is similar to that described in connection with FIG. 2 or FIG. 3. The discharge lamp includes in particular a lens 4 arranged on the axis of the hollow cylindrical anode 15, forming a first optical path towards the first zone 11 of the sample 10, which is exposed to the glow discharge plasma at the end of the anodic tube. The anode also includes another off-axis opening, for example in a plane XZ, aligned on a cylindrical opening in the intermediate part 16 so as to form a second optical path towards the second zone 12 of the sample. In FIG. 4, the second zone 12 does not appear, because it is located in a plane transverse to the plane of FIG. 4.

On the one hand, the lens 4 focuses the first incident beam 21 on the first zone 11 of the sample, that is opposite to the tubular end of the anode 15 and that is exposed to the etching plasma. On the other hand, the lens 4 focuses the second incident beam 22 on the second zone 12 of the sample via the second optical path that passes through the anode 15 through an off-axis optical window 14 and through the intermediate part 16 through an off-axis opening 17. The second zone 12 of the sample is hence protected from the etching plasma.

The first incident beam 21 forms by reflection on the first zone 11 a reflected beam 31, that is inclined symmetrically to the incident beam with respect to the normal to the sample. Similarly, the second incident beam 22 forms, by reflection on the second zone 12, a reflected beam 32 that is inclined symmetrically to the incident beam with respect to the normal to the sample. Hence, the reflected beam 31 propagates along an optical path angularly separated from the incident beam 21. Likewise, the reflected beam 32 propagates along an optical path angularly separated from the incident beam 22. Moreover, the first and the second reflected beams are spatially separated and propagate in the discharge lamp along spatially distinct optical paths.

The lens 4 collects the first reflected beam 31 and the second reflected beam 32, which appear superimposed to each other in FIG. 4, but are in reality offset in a plane YZ. The mirror 24 reflects the first and second reflected beams 31, 32 towards a beam-combining prism 23. The lens 4 focuses the first and second reflected beams 31, 32 on the beam combiner 23, so as to geometrically superimpose them.

The beam combiner 23 optically recombines the first and second reflected beams 31, 32 and hence forms an interferometric beam 30 towards the source-detector block 50. The source-detector block includes a filter 18, for example of the interferometric filter type, which allows eliminating the spurious emission of the plasma or of the ambient light.

The detection system of FIG. 4 is different from those described in connection with FIGS. 1 and 3 in that it includes a polarimetric detection system. More precisely, this polarimetric detection system includes a non-polarizing splitter 51, a first polarization splitter 52 and a second polarization splitter 53, a quarter-wave plate 54, a polarization rotator 33 and four detectors 81, 82, 83, 84. In an alternative embodiment, the positions of the elements 54 and 33 may be inverted.

Advantageously, the non-polarizing splitter 51 will preserve at best the polarization state of the incident beam both on the transmitted and reflected paths. For this reason, the non-polarizing splitters for laser, optimized for a narrow wavelength range will be preferable to the wide-band splitters, covering for example the whole visible spectrum.

The polarization rotator 55 associated with the polarization splitter 52 forms an analyser of linear polarizations oriented at 45° with respect to the axes of the recombiner splitters 13 and 23. The detector 81 detects a polarization component 35 of the interferometric beam 30 at +45° and the detector 82 detects a polarization component 37 of the interferometric beam 30 at −45° with respect to the axes 13 and 23.

The quarter-wave plate 54 associated with the polarization splitter 53 forms an analyser of circular polarizations, respectively right circular 36 and left circular 38. The detector 83 detects the right circular polarization component 36 of the interferometric beam 30 and the detector 84 detects the left circular polarization component 38 of the interferometric beam 30.

Hence, the detection system of FIG. 4 allows detecting simultaneously the four polarization components of the interferometric beam 30.

Based on the four signals detected by the four detectors 81, 82, 83, 84, it is possible to deduce the phase-shift between the beam 31 reflected by the first zone 11, i.e. in the crater resulting from the etching of the sample, and the beam 32 reflected by the second zone 12, which serves as a reference. Likewise, the variation of the reflection coefficient of the first zone may be calculated based on the measurement of the two linear polarization components or the two circular polarization components.

The analysis of the interferometric signals is based on the conventional approach. In the case where the sample is consisted of an homogeneous and absorbent material, it may be made the hypothesis of a semi-infinite medium. In the case where the sample includes a stack of thin and/or transparent layers at the measurement wavelength, the analysis is based on numerical calculations of simulation and minimization of an error function.

A measurement system as illustrated in FIG. 4 provides four simultaneous measurements as a function of time. All the measurements of the four detectors provide by interpolation four curves that may be analysed either in real time, for an homogeneous sample, or after the acquisition of all the measurements, for a sample including a stack of layers. Knowing the coefficients of optical refraction and absorption of a material at the measurement wavelength, it is possible to model the intensity and the phase of the interferometric beam as a function of the etching rate and the time. By integrating the etching rate, it is obtained the etching depth in the sample as a function of time t.

The analysis of these curves allows deducing therefrom a measurement of the etching rate in a material or a layer. The occurrence of a discontinuity on a curve allows detecting the etching of an interface between two layers or two different materials in a sample.

More precisely, let's note $I_{L1}$ the intensity of the linear component of the interferometric beam along a direction at 45 degrees with respect to the linear polarization H of the field incident on the first zone 11 and with respect to the linear polarization V of the field incident on the second zone 12. The detector 81 measures the intensity of the beam 35, i.e.

Let's note $I_{L2}$ the intensity of the linear component of the interferometric beam in a direction of −45 degrees with respect to the linear polarization H of the field incident on the first zone 11 and with respect to the linear polarization V of the field incident on the second zone 12. The detector 82 measures the intensity of the beam 37, i.e. $I_{L2}$.

Let's note the intensity of the right circular component of the interferometric beam. The detector 83 measures the intensity of the beam 36, i.e.

Let's note $I_{C2}$ the intensity of the left circular component of the interferometric beam. The detector 84 measures the intensity of the beam 38, i.e. $I_{C2}$.

The normalized intensity difference L between the intensities detected on the linear paths is calculated:

$$L = \frac{I_{L_1} - I_{L_2}}{I_{L_1} + I_{L_2}} = \frac{2E_V E_H \rho_V \rho_H \cos(\delta)}{E_V^2 \rho_V^2 + E_H^2 \rho_H^2}$$

Likewise, the normalized intensity difference C between the intensities detected on the circular paths is calculated:

$$C = \frac{I_{C_2} - I_{C_1}}{I_{C_2} + I_{C_1}} = \frac{2E_V E_H \rho_V \rho_H \sin(\delta)}{E_V^2 \rho_V^2 + E_H^2 \rho_H^2}$$

It is shown that the phase difference between the reflected waves 31 and 32 is written:

$$\delta(t) = \arctan\left(\frac{I_{C_2} - I_{C_1}}{I_{C_2} + I_{C_1}} \cdot \frac{I_{L_1} + I_{L_2}}{I_{L_1} - I_{L_2}}\right)$$

The variation of the reflectivity R(t) of the crater over time may also be deduced from the measurement of the two linear components $I_{L1}$ and $I_{L2}$ (or as a variant, based on the two circular components $I_{C1}$ and $I_{C2}$), knowing the intensity of the two chosen paths at t=0, is expressed by the following relation:

$$R(t) \propto I_{L_1}(t) + I_{L_2}(t) - \left(\frac{I_{L_1}(0) + I_{L_2}(0)}{2}\right)$$

As an alternative, the angle ψ may be defined such that $\tan(\psi) = \rho_H/\rho_V$. The variations of reflectivity $\rho_H/\rho_V$ may then be deduced based on the measurements by the relation $\sin^2(2\psi) = C^2 + L^2$.

Thick and Opaque Layers

In the case of a sample or a layer of opaque material, the depth d(t) of the etched crater is obtained based on the phase variation as a function of time with respect to the initial value:

$$d(t) = \frac{\lambda}{4\pi}[\delta(t) - \delta(0)] = \frac{\lambda}{4\pi}\left[\arctan\left(\frac{C(t)}{L(t)}\right) - \arctan\left(\frac{C(0)}{L(0)}\right)\right]$$

Hence, the measurement of the intensities of the four polarization components allows deducing directly the depth d(t) of the crater as a function of the time of exposure to the etching plasma.

The local slope of d(t) indicates the instantaneous etching rate.

The reflectivity is linked to the index of the sample surface.

The second embodiment has for advantage to allow accessing directly to the phase difference between the two waves without needing a sinusoidal fit, generally very little accurate when the etching depth d(t) is lower than one period.

Thin or Transparent Layers

If the sample includes a stack of layers of a transparent material, such as silica or absorbent but not very thick layers, as in the case of hard disks, there exists no simple relation between etched depth and phase difference. Indeed, the beams reflected on the sample undergo multiple reflections at the interfaces between the different layers. The detected interferometric beam is the result of the superimposition of all these reflections. The detected interferometric beam is modulated in phase and in intensity during the etching.

In the presence of transparent or very thin layers, the estimation of the depth is then based on a numerical model of the sample constructed from the knowledge of the materials constituting the different layers. This model takes into account the multiple reflections of the laser beams at the sample and allows calculating the phase and the reflectivity of the reflected waves at each instant of the etching.

The phase and the reflectivity of the reflected wave are calculated by considering the propagation of the wave in the sample, which may be described by a matrix formalism (see, for example, P. Yeh, Optical waves in layered media, 1988, Wiley).

The analysis of the etching of a sample is then based on calculations of simulation of the numerical model, on a comparison with the measurements of intensity of the different polarization components as a function of time and on a minimization of the difference between the calculations of simulation and the measurements. For example, the minimization may be used on a least square regression using as an adjustable parameter the etching rate of each layer, to allow estimating by successive approximations the values that give the phase and reflectivity curves that adapt the best to the experimental ones. The least square regression may be performed by minimization of the difference between the theoretical and experimental curves either of the phase only, or of the reflectivity only, or of the phase and the reflectivity at the same time. It is also possible to choose different minimizations for each layer. The choice between these different variants generally depends on the structure of the sample analysed and of the characteristics of the layers analysed.

A difference between the calculations and the measurements allows refining the numerical model and detecting for example the presence of intermediate layers, which have a gradient of index between two superimposed materials.

The results of so-obtained interferometric measurements and results of ellipsometric measurements taken on the same samples have been compared. The thicknesses obtained by polarimetric interferometry (device according to the second embodiment) and by ellipsometry are very close, the difference between the measurements by polarimetric interferometry (under almost-normal incidence) and by ellipsometry being generally lower than 5%.

The interferometric measurement system, preferably polarimetric, hence allows measuring the etching depth $d(t)$ in the sample as a function of the duration of exposure to the etching plasma. It is hence possible to evaluate the etching rate of each sample, and more precisely the etching rate of each layer of a sample formed of a stack of layers.

It hence becomes possible to correct the detected emission spectrometry measurements as a function of the etching time t, for analysing and representing them as a function of the etching depth in the sample.

Advantageously, the etching depth measurement detailed hereinabove applies to a plasma operating in impulsive or pulsed mode. The pulsed mode is commonly used to avoid excessively heating a fragile sample, comprising for example a material or a layer of polymer. In pulsed mode, the plasma is alternately switched-on then switched-off with predetermined frequency and duty factor. The erosion occurs only during the phase in which the plasma is switched-on.

Two embodiments are herein contemplated more particularly to improve the etching depth measurement accuracy.

In a first case, permanent sources of disturbance may be at the origin of the signal drifts during the on and off plasma phases. In this case, it is measured the residual drift of the interferometric signal in the off plasma phases, where there is no etching, and where only a drift of the signal is hence measured. It is hence possible to correct these drifts by interpolating them in the on plasma phases.

In another case, intermittent sources of disturbance are at the origin of specific residual drifts only during the on plasma phase, for example drifts thermally induced by the plasma. In this case, the interferometric signal is measured only during the off plasma phases, in which there is no drift of the signal. These interferometric signal measurements are used during the off plasma phases to deduce therefrom, for example by interpolation, the etching depth as a function of time.

The choice of either one of the methods exposed hereinabove depends on the relative amplitude of the permanent and intermittent drifts.

The system of the invention hence allows providing measurements by glow discharge spectrometry as a function of a reliable measurement of the etching depth $d(t)$ in a sample, and not only as a function of time.

The acquisition of the interferometric signals is performed in situ and simultaneously with the acquisition of the measurements by emission spectrometry or mass spectrometry. The measurement system illustrated in connection with FIG. 4 allows determining accurately the etching depth in a sample or in the layers of a sample as a function of the time of exposure to the etching plasma.

The combination of the optical emission (or mass) spectrometry and the interferometric measurement allows relating extremely accurately the analysis of the elementary composition of a sample to the etching depth in this sample.

The interferometric measurement system of the invention is not very sensitive to the mechanical noise, for example of the vacuum pump devices, and not very sensitive to the thermal drifts inducted by the heating due to the ablation plasma.

The invention claimed is:

1. A system of glow discharge spectrometry and in situ measurement of the etching depth of a sample, comprising:
    a glow discharge lamp adapted to receive a solid sample and to form a glow discharge etching plasma, the sample having, on a same face, a first zone exposed to the etching plasma and a second zone protected from the etching plasma;
    a spectrometer coupled to the glow discharge lamp, the spectrometer being adapted to measure, as a function the time of exposure of the first zone to said plasma, at least one signal representative of the glow discharge plasma by optical emission spectrometry and/or by mass spectrometry;
    a system of in situ measurement of the depth of an erosion crater generated by etching of the first zone of the sample as a function of the time of exposure to said plasma;

wherein the system of measurement of the erosion crater depth includes:
a light source adapted to emit a light beam;
an optical splitter adapted to spatially or angularly split the light beam into a first incident beam and a second incident beam;
the glow discharge lamp being adapted to provide a first optical path towards the first zone and a second optical path towards the second zone of the sample, the glow discharge lamp including an anode having a first axial opening and a second opening, offset with respect to the axis of the anode;
optical means adapted to direct, respectively, the first incident beam towards the first zone along the first optical path and the second incident beam towards the second zone along the second optical path, so as to form a first reflected beam by reflection on the first zone and, respectively, a second reflected beam by reflection on the second zone, the first axial opening being adapted for the passage of the first incident beam and of the first reflected beam and, respectively, the second opening being adapted for the passage of the second incident beam and of the second reflected beam;
a beam splitter adapted to recombine the first reflected beam and the second reflected beam and to form an interferometric beam;
detection means adapted to receive the interferometric beam and to detect an interferometric signal as a function of the time of exposure of the first zone to said plasma; and
processing means adapted to process the interferometric signal so as to determine the depth (d) of the erosion carter as a function of the time of exposure of the first zone to said plasma.

2. The glow discharge spectrometry system according to claim 1, wherein the detection means and the processing means are adapted to process the interferometric signal and to extract therefrom a measurement of the amplitude (A) and of the phrase (PHI) of the interferometric signal as a function of the time of exposure of the first zone to said plasma.

3. The glow discharge spectrometry system according to claim 1, wherein the first incident beam forms an angle of incidence lower than ten degrees with respect to the normal to the surface of the first zone of the sample.

4. The glow discharge spectrometry system according to claim 3, wherein the sample forms cathode of the discharge lamp and wherein the second opening is provided with an optical window adapted for the passage of the second incident beam and of the second reflected beam.

5. The glow discharge spectrometry system according to claim 3, wherein the optical separator and the beam splitter are merged together.

6. The glow discharge spectrometry system according to claim 1, wherein the sample forms cathode of the discharge lamp and wherein the second opening is provided with an optical window adapted for the passage of the second incident beam and of the second reflected beam.

7. The glow discharge spectrometry system according to claim 6, wherein the spectrometer comprises a mass spectrometer coupled to the discharge lamp via an opening, the mass spectrometer being adapted to measure at least one signal representative of ionised species of the glow discharge plasma by mass spectrometry.

8. The glow discharge spectrometry system according to claim 6, wherein the spectrometer comprises an optical spectrometer coupled to the discharge lamp via an optical window or via a lens optical system, the optical spectrometer being adapted to measure at least one optical emission signal representative of excited species of the glow discharge plasma, preferably in a direction normal to the surface of the first zone of the sample.

9. The glow discharge spectrometry system according to claim 6, wherein the glow discharge spectrometry system includes an optical spectrometer adapted to measure at least one optical emission signal representative of excited species of the glow discharge plasma, and wherein the light source is adapted to emit a light beam at a wavelength selected outside of a range of wavelengths of atomic rays of optical emission of the glow discharge plasma.

10. The glow discharge spectrometry system according to claim 1, wherein the optical separator comprises at least one polarization-splitting prism.

11. The glow discharge spectrometry system according to claim 10, wherein the optical separator comprises a Wollaston prism and the beam splitter comprises another Wollaston prism, and wherein the optical means adapted to direct, respectively, the first incident beam towards the first zone and the second incident beam towards the second zone comprise a lens optical system, said Wollaston prisms being arranged in the focal plane of the lens optical system.

12. The glow discharge spectrometry system according to claim 1, wherein the optical separator and the beam splitter ice are merged together.

13. The glow discharge spectrometry system according to claim 1, wherein the spectrometer comprises a mass spectrometer coupled to the discharge lamp via an opening, the mass spectrometer being adapted to measure at least one signal representative of ionised species of the glow discharge plasma by mass spectrometry.

14. The glow discharge spectrometry system according to claim 1, wherein the spectrometer comprises an optical spectrometer coupled to the discharge lamp via an optical window or via a lens optical system, the optical spectrometer being adapted to measure at least one optical emission signal representative of excited species of the glow discharge plasma, preferably in a direction normal to the surface of the first zone of the sample.

15. The glow discharge spectrometry system according to claim 1, wherein the glow discharge spectrometry system includes an optical spectrometer adapted to measure at least one optical emission signal representative of excited species of the glow discharge plasma, and wherein the light source is adapted to emit a light beam at a wavelength selected outside of a range of wavelengths of atomic rays of optical emission of the glow discharge plasma.

16. The glow discharge spectrometry system according to claim 1, wherein the detection means comprise a polarimeter adapted to measure at least one polarized component of the interferometric beam.

17. The glow discharge spectrometry system according to claim 16, wherein said polarimeter comprises other optical separation means arranged so as to split the interferometric beam into a plurality of polarized components and a plurality of detectors adapted to each detect respectively a polarized component of the plurality of polarized components of the interferometric signal.

18. A method of glow discharge spectrometry and in situ measurement of the etching depth of a sample, comprising the following steps:
placing a solid sample into a glow discharge lamp, the glow discharge lamp including an anode having a first axial opening and a second opening, offset with respect to the axis of the anode, the sample having, on a same face, a first zone exposed to an etching plasma and a second zone protected from the etching plasma;

detecting and analysing, by optical emission spectrometry and/or by mass spectrometry, of at least one signal representative of excited and/or ionized species of the glow discharge plasma, as a function of the time of exposure of the first zone to said plasma;

emitting a light beam;

spatial or angular splitting of the light beam into a first incident beam and a second incident beam;

orienting, respectively, the first incident beam towards the first zone along a first optical path passing through the first axial opening of the anode and a second incident beam towards the second zone along a second optical path passing through the second opening of the anode, so as to form a first reflected beam by reflection on the first zone, the first reflected beam passing through the first axial opening of the anode and, respectively, a second reflected beam by reflection on the second zone, the second reflected beam passing through the second opening of the anode, optically recombining the first reflected beam and of the second reflected beam and to form an interferometric beam;

detecting the interferometric beam to form at least one interferometric signal as a function of the time of exposure of the first zone to said plasma; and processing of the at least one interferometric signal to extract therefrom a measurement of an erosion crater depth as a function of the time of exposure of the first zone to said plasma.

19. The method of glow discharge spectrometry and in situ measurement of the etching depth of a sample according to claim 18, further including the following steps:

processing of the interferometric signal to extract therefrom a measurement of the phase (PHI) of the interferometric signal as a function of the time of exposure of the first zone to said plasma;

determining, at each instant t, an instantaneous etching rate $V_e$ of the first zone of the sample, by application of the following formula:

$$V_e = \frac{LAMBDA}{4 \times \pi} \times \frac{dPHI}{dt}$$

where LAMBDA represents the wavelength of the light source and dPHI/dt the derivative with respect to time of the phase (PHI) of the interferometric signal measured.

20. The method of glow discharge spectrometry and in situ measurement of the etching depth of a sample according to claim 18, wherein the etching plasma operates in a pulsed mode, by alternation of a phase in which the plasma is switched-on and another phase in which the plasma is switched-off, and comprising the following steps:

detecting the at least one interferometric signal triggered during the phases in which the plasma is switched-on and/or, respectively, during the phases in which the plasma is switched-off, so as to differentiate an interferometric signal associated with the phases in which the plasma is switched-on from another interferometric signal associated with the phases in which the plasma is switched-off, processing of the interferometric signal associated with the phases in which the plasma is switched-on and/or, respectively, of the other interferometric signal associated with the phases in which the plasma is switched-off so as to correct the measurement of the erosion crater depth from the drifts induced during the phases in which the plasma is switched-on and/or, respectively, during the phases in which the plasma is switched-off.

* * * * *